(12) United States Patent
Maruyama (10) Patent No.: US 7,828,725 B2
(45) Date of Patent: Nov. 9, 2010

(54) BENT STATE HOLDING MECHANISM OF AN ENDOSCOPE

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 798 days.

(21) Appl. No.: 11/737,305

(22) Filed: Apr. 19, 2007

(65) Prior Publication Data

US 2007/0255104 A1 Nov. 1, 2007

(30) Foreign Application Priority Data

Apr. 26, 2006 (JP) ............... 2006-121597
Feb. 8, 2007 (JP) ............... 2007-028708

(51) Int. Cl.
*A61B 1/00* (2006.01)
(52) U.S. Cl. ............... 600/148; 600/146; 600/147
(58) Field of Classification Search .......... 600/143–149
See application file for complete search history.

(56) References Cited

U.S. PATENT DOCUMENTS

| 5,329,887 | A | * | 7/1994 | Ailinger et al. | ............. | 600/148 |
| 5,496,260 | A | * | 3/1996 | Krauter et al. | ............. | 600/148 |
| 5,507,717 | A | * | 4/1996 | Kura et al. | ............. | 600/146 |
| 2001/0037051 | A1 | * | 11/2001 | Fujii et al. | ............. | 600/146 |

FOREIGN PATENT DOCUMENTS

| JP | 9-98942 | 4/1997 |
| JP | 10-286220 | 10/1998 |
| JP | 2005-160791 | 6/2005 |

OTHER PUBLICATIONS

U.S. Appl. No. 11/737,291 to Maruyama, filed Apr. 19, 2007.
U.S. Appl. No. 11/737,331 to Maruyama, filed Apr. 19, 2007.
An English language Abstract and English language computer-generated translation of JP 9-98942.
An English language Abstract and English language computer-generated translation of JP 10-286220.
An English language Abstract and English language computer-generated translation of JP 2005-160791.

* cited by examiner

*Primary Examiner*—Linda C Dvorak
*Assistant Examiner*—Ryan Henderson
(74) *Attorney, Agent, or Firm*—Greenblum & Bernstein P.L.C.

(57) ABSTRACT

A bent state holding mechanism for an endoscope which includes a control portion and an insertion portion extending therefrom, the insertion portion having a bendable portion at a distal end thereof, including a bendable portion control mechanism provided on the control portion, which is operated to bend the bendable portion, and at least two frictional resistance producing members which rotate relative to each other upon operation of the bendable portion control mechanism, to exert a frictional resistance for holding the bendable portion at any operated position. The two frictional resistance producing members include a radial plate spring made of resilient metal which includes a ring portion and a plurality of radial projections which project radially outwards from the ring portion; and an annular friction member having a pressure surface which is brought to be pressed obliquely against flat surfaces of the plurality of radial projections.

13 Claims, 10 Drawing Sheets

BENT STATE HOLDING MECHANISM OF AN ENDOSCOPE

BACKGROUND OF THE INVENTION

1. Field of the Invention

The present invention relates to a bent state holding mechanism of an endoscope.

2. Description of the Related Art

In typical endoscopes, a bendable portion control mechanism for bending the bendable portion, which is provided in the vicinity of the distal end of the insertion portion of the endoscope, by remote control is freely rotatably mounted to the control portion that is coupled to the proximal end of the insertion portion of the endoscope, and such endoscopes are provided with a bent state holding mechanism for holding the bendable portion control mechanism at any given rotation position by exerting frictional resistance on the rotating operation of the bendable portion control mechanism so that the free end of the insertion portion of the endoscope remains directed toward a target affected area, or the like.

The bent state holding mechanism of such conventional endoscopes is provided with frictional resistance producing members which exert frictional resistance on the rotating operation of the bendable portion control mechanism. Such frictional resistance producing members are made from a doughnut-shaped frictional disk made of a soft material such as rubber or cork and a metal disk which is pressed against the entire surface of the frictional disk on one side thereof. This structure is disclosed in, e.g., Japanese patent publications H09-98942 and Japanese patent publication 2005-160791.

However, if such a frictional disk that is made of a soft material such as rubber or cork is used as one frictional resistance producing member of the bent state holding mechanism, a second metal disk or the like needs to be provided on the back of the frictional disk to support the frictional disk; moreover, a disk spring or the like needs to be provided or the frictional disk of a soft material needs to be formed to have a sufficient thickness.

Consequently, the bent state holding mechanism of the conventional endoscope becomes great in thickness, which increases the size of a bendable portion control knob of the endoscope if the bent state holding mechanism is installed in an internal space of the bendable portion control knob to thereby deteriorate the operability thereof, and which sometimes makes it difficult for another mechanism (e.g., a torque limiting mechanism for preventing a torque exerted on the bendable portion control knob from being transmitted to the bendable portion for safety when the torque exceeds a predetermined torque) to be installed in an internal space of the bendable portion control knob if so desired.

In addition, the frictional disk made of rubber, cork or the like cannot be formed in a precise flat shape, which causes only a radially outer portion or a radially inner portion of the frictional disk to be pressed against the metal disk, and accordingly, the magnitude of the frictional resistance which occurs by pressure contact of the frictional disk with the metal disk varies greatly.

Additionally, the frictional disk made of rubber, cork or the like is vulnerable to heat and easy to deteriorate with time, so that a prescribed magnitude of frictional resistance may not be obtained over a long period of time if high-temperature steam under pressure sterilization is repeated after each use of the endoscope.

Additionally, in the bent state holding mechanism of the endoscope, the operability of the endoscope is enhanced if the bendable portion can be bent simply by performing a bendable portion control operation (i.e., without requiring to perform an operation releasing the application of frictional resistance to the rotating operation of the bendable portion control mechanism) after the bendable portion control mechanism has been stopped and held at any given rotational position by a frictional resistance exerted on the rotating operation of the bendable portion control mechanism by the bent state holding mechanism and if the bendable portion control mechanism can be stopped and held at another rotation position once this bending portion control operation is stopped. However, since dynamic friction of rubber, cork, or the like, is unstable and often becomes greater than static friction thereof, the bendable portion becomes very heavy when it is operated unless the application of frictional resistance is released in conventional bent state holding mechanisms, which deteriorates the operability of the endoscope.

SUMMARY OF THE INVENTION

The present invention provides a bent state holding mechanism of an endoscope which can be made small in thickness and size, which consequently makes it possible to improve the operability of the endoscope by the miniaturization of the bendable portion control knob and possible to install another mechanism in an internal space of a bendable portion control knob. Furthermore, the magnitude of frictional resistance produced by the bent state holding mechanism does not vary greatly, and the bent state holding mechanism is superior in heat resistance and resistance to aged deterioration. Hence, excellent operability of the endoscope is achieved.

According to an aspect of the present invention, a bent state holding device is provided for an endoscope which includes a control portion and an insertion portion extending from the control portion, the insertion portion having a bendable portion at a distal end thereof, including a bendable portion control mechanism provided on the control portion, which is operated to bend the bendable portion, and at least two frictional resistance producing members which rotate relative to each other upon operation of the bendable portion control mechanism, to exert a frictional resistance for holding the bendable portion at any operated position. The two frictional resistance producing members include a radial plate spring made of resilient metal which includes a ring portion and a plurality of radial projections which project radially outwards from the ring portion; and an annular friction member having a pressure surface which is brought to be pressed obliquely against flat surfaces of the plurality of radial projections.

It is desirable for the radial plate spring to be formed in a flat shape as a whole, and for the pressure surface of the annular friction member to be formed in an umbrella-like beveled shape.

It is desirable for the radial plate spring to be formed in an umbrella-like beveled shape as a whole, and for the pressure surface of the annular friction member to be formed in a flat shape.

It is desirable for at least edges of the plurality of radial projections which are pressed against the pressure surface of the annular friction member to be chamfered.

It is desirable for the radial plate spring to rotate with the bendable portion control mechanism about an axis of rotation, and for the annular friction member to be engaged with a fixing member of the control portion to be prevented from rotating relative to the control portion.

It is desirable for the bent state holding mechanism to include a bent state holding device which is operated to switch between an engaged state in which the plurality of radial projections and the pressure surface of the annular friction member are pressed against each other and a disengaged state in which the plurality of radial projections and the pressure surface of the annular friction member are disengaged from each other.

It is desirable for the amount of pressure contact between the plurality of radial projections and the annular friction member to be varied by an operation of the bent state holding device.

As the amount of pressure contact between the plurality of radial projections and the annular friction member increases, it is desirable for the plurality of radial projections to be resiliently deformed by a greater amount while the area on portions of the plurality of radial projections which are pressed against the pressure surface of the annular friction member gradually increases in radially inward directions from radially outermost portions of the plurality of radial projections.

It is desirable for the bendable portion control mechanism to include a bendable portion control knob for controlling the bendable portion, the bent state holding mechanism being installed in an internal space of the bendable portion control knob.

It is desirable for the annular friction member to be a metal disk.

It is desirable for the endoscope to include a control wire, a distal end of which is fixed to the bendable portion and which is extended to the control portion through the insertion portion.

It is desirable for the bendable portion control device to include a torque limiting mechanism for allowing a torque exerted on the bendable portion control mechanism to be transmitted to the bendable portion when the torque is equal to or less than a predetermined torque, and for preventing the torque from being transmitted to the bendable portion when the torque exceeds the predetermined torque, the torque limiting mechanism being installed in an internal space of the bendable portion control knob.

It is desirable for the bendable portion control mechanism to include a bendable portion control knob for controlling the bendable portion, and for the bent state holding device includes a bent state holding knob positioned so as to be capable of being operated to rotate coaxially with the bendable portion control knob.

According to the present invention, since the frictional resistance producing members are made from a radial plate spring and a metal disk, wherein the radial plate spring is made of resilient metal which includes a ring portion and a plurality of radial projections that project radially outwards from the ring portion, and wherein the metal disk has a pressure surface which is brought to be pressed obliquely against flat surfaces of the plurality of radial projections, the bent state holding mechanism can be made small in thickness and size, which consequently makes it possible to improve the operability of the endoscope by the miniaturization of the bendable portion control knob and possible to install another mechanism in an internal space of a bendable portion control knob. Furthermore, the magnitude of frictional resistance produced by the bent state holding mechanism does not vary greatly, and the bent state holding mechanism is superior in heat resistance and resistance to age deterioration. Hence, excellent operability of the endoscope is achieved.

The present disclosure relates to subject matter contained in Japanese Patent Applications No. 2006-121597 (filed on Apr. 26, 2006) and No. 2007-28708 (filed on Feb. 8, 2007), which are expressly incorporated herein in their entireties.

BRIEF DESCRIPTION OF THE DRAWINGS

The present invention will be described below in detail with reference to the accompanying drawings in which.

DESCRIPTION OF THE PREFERRED EMBODIMENTS

Figure 2:
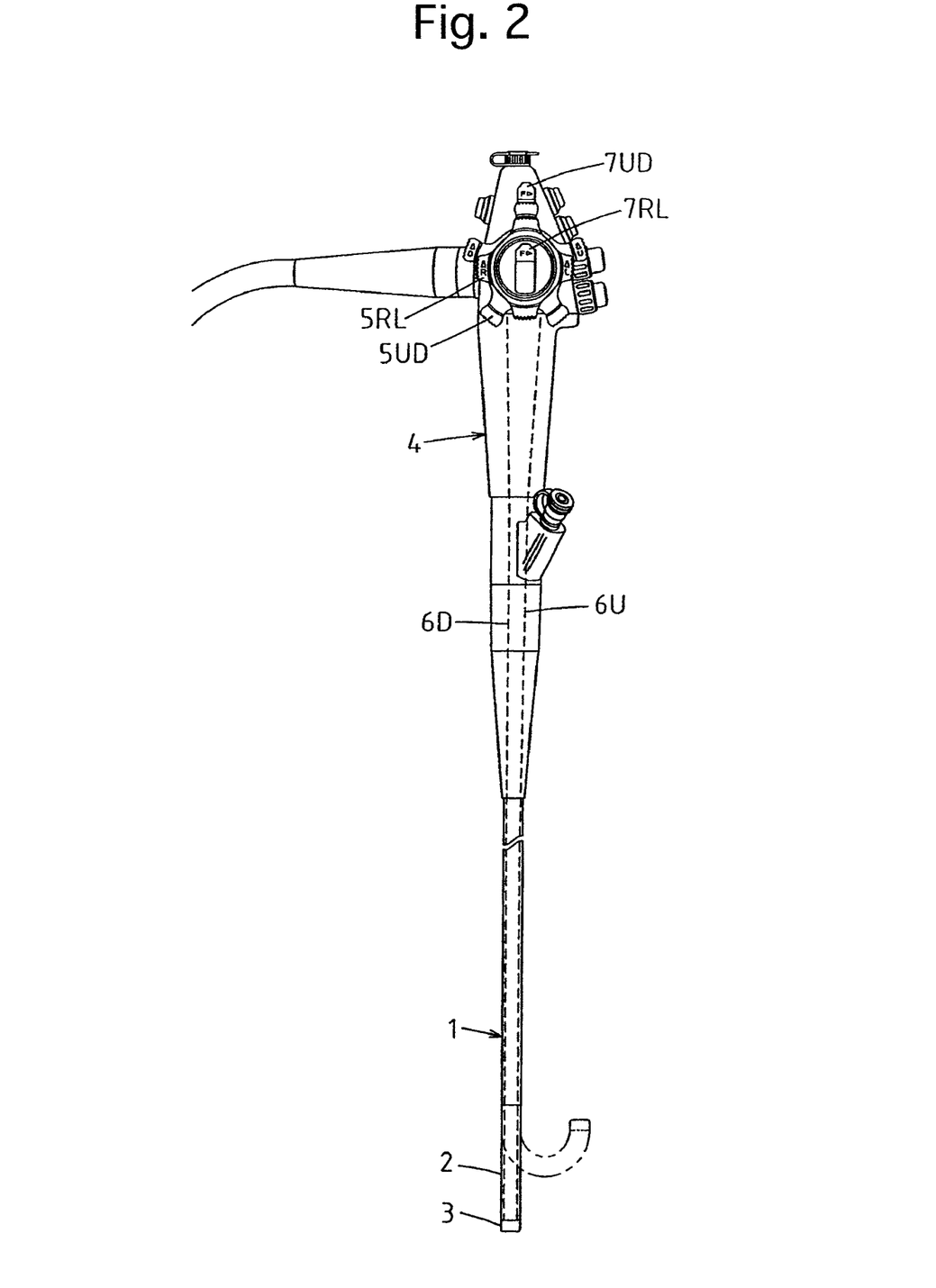
FIG. 2 is an external view of the endoscope, showing the overall structure thereof.

FIG. 2 shows the general configuration of a first embodiment of the endoscope. The endoscope is provided with a flexible insertion portion 1 and a control portion 4 coupled to the proximal end of the insertion portion 1. The insertion portion 1 is provided in the vicinity of the distal end (free end) thereof with a remote-controllable bendable portion 2, and is further provided with an end body 3 fixed to the end (free end) of the bendable portion 2. An objective window and others (not shown) are provided in the end body 3.

The control portion 4, which is coupled to the proximal end of the insertion portion 1, is provided thereon with a U-D control knob 5UD for bending the bendable portion 2 upward and downward and an R-L control knob 5RL for bending the bendable portion 2 rightward and leftward. The U-D control knob 5UD and the R-L control knob 5RL are overlaid on each other and coaxially arranged so that each of the U-D control knob 5UD and the R-L control knob 5RL can be freely rotated on a common axis.

An upward-direction control wire 6U and a downward-direction control wire 6D are inserted into the insertion portion 1 and distal ends thereof and are fixed to the end body 3. Turning the U-D control knob 5UD counterclockwise causes the upward-direction control wire 6U to be pulled toward the control portion 4 to thereby cause the bendable portion 2 to bend upward (e.g., upward direction of a monitoring screen which corresponds to forward direction of the control portion 4) as shown by two-dot chain lines in FIG. 2. Turning the U-D control knob 5UD clockwise causes the downward-direction control wire 6D to be pulled toward the control portion 4 to thereby cause the bendable portion 2 to bend downward. The distal ends of the upward-direction control wire 6U and the downward-direction control wire 6D are fixed to the end body 3.

Additionally, turning the R-L control knob 5RL counterclockwise causes a leftward-direction control wire 6L, which is inserted into the insertion portion 1 to be installed therein, to be pulled toward the control portion 4 to thereby cause the bendable portion 2 to bend leftward. Turning the R-L control knob 5RL clockwise causes a rightward-direction control wire 6R, which is installed in the insertion portion 1, to be pulled toward the control portion 4 to thereby cause the bendable portion 2 to bend rightward. In this manner, the bendable portion 2 can be remote-controlled to be bent freely in any directions at any angle from the control portion 4 side.

The control portion 4 is provided with a U-D bent state holding knob (bent state holding device) 7UD which is operated to hold the U-D control knob 5UD at any given rotation position and a R-L bent state holding knob 7RL which is operated to hold the R-L control knob 5RL at any given rotation position. The U-D bent state holding knob 7UD and the R-L bent state holding knob 7RL are arranged to be capable of being operated to rotate coaxially with the U-D control knob 5UD and the R-L control knob 5RL.

Figure 1:
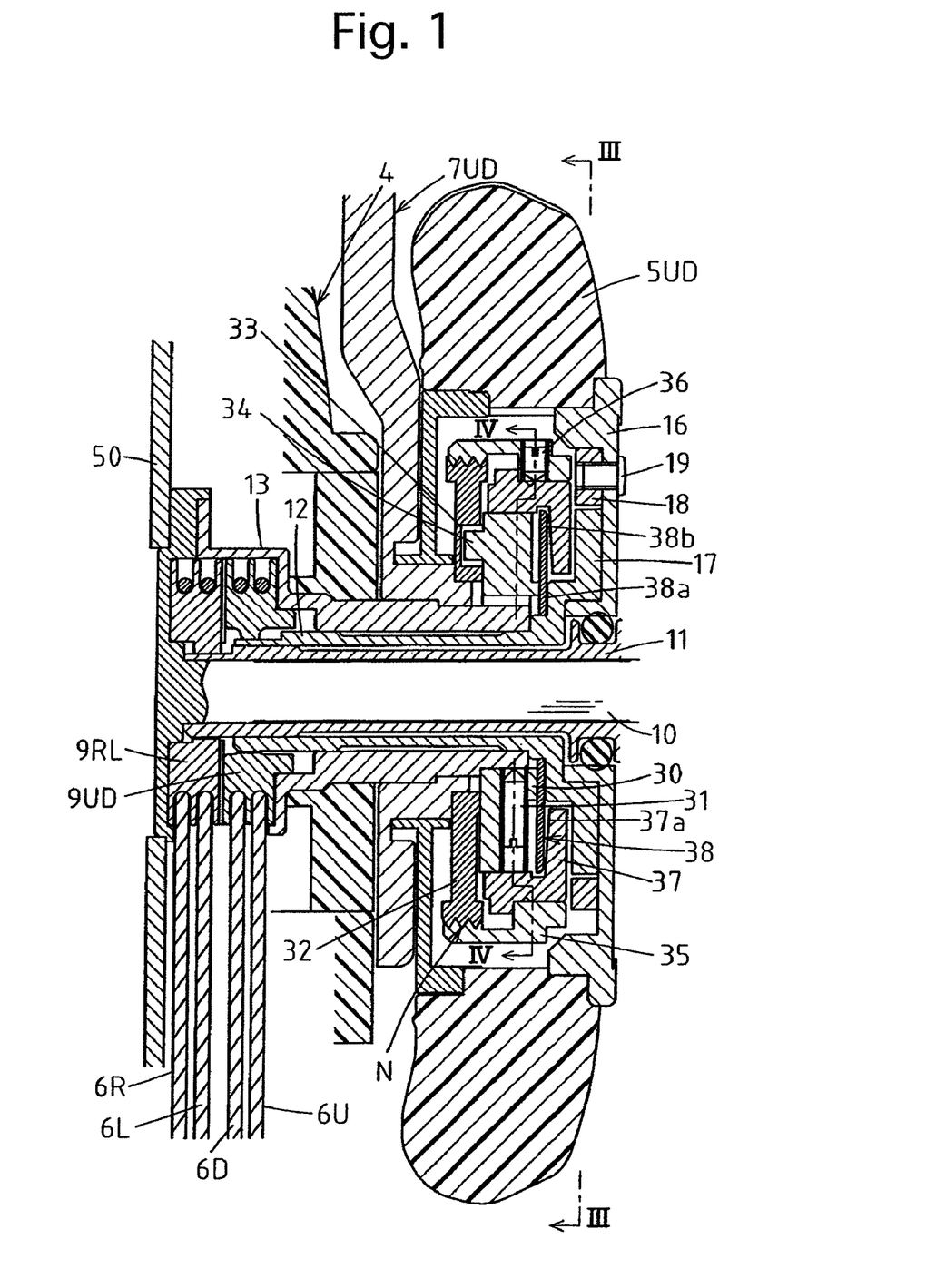
FIG. 1 is a longitudinal cross sectional view of an embodiment of a portion of an endoscope according to the present invention, showing a bent state holding mechanism of the endoscope.

FIG. 1 shows a bendable portion U-D control mechanism, installed to the control portion 4 in a freely rotatable manner, for bending the bendable portion 2 vertically. The U-D control knob 5UD is formed so that a ring-shaped control portion thereof has a large internal space, and a supporting column (cylindrical shaft) 10 of the operating force transmission mechanism is fixed to an internal main frame 50 of the control portion 4 to extend upright coaxially with the axis of the U-D control knob 5UD.

As shown in FIG. 1, the operating force transmission mechanism is provided with a U-D pulley having two outer peripheral grooves in which the upward-direction control wire 6U and the downward-direction control wire 6D are engaged and wound around the U-D pulley 9UD by a half to one turn and extend therefrom toward the bendable portion 2. The operating force transmission mechanism is also provided with an R-L pulley 9RL similar in structure to the U-D pulley 9UD, having two outer peripheral grooves in which the leftward-direction control wire 6L and the rightward-direction control wire 6R are engaged to be wound around the R-L pulley 9RL by a half to one turn and extend therefrom toward the bendable portion 2.

An R-L tubular drive shaft 11 fixed at one end thereof to the R-L pulley 9RL is rotatably fitted on the supporting column 10 and a U-D tubular drive shaft 12 fixed at one end thereof to the U-D pulley 9UD is rotatably fitted on the R-L tubular drive shaft 11. In order to transmit rotations of the R-L control knob 5RL and the U-D control knob 5UD to the R-L pulley 9RL and the U-D pulley 9UD, the R-L tubular drive shaft 11 and the U-D tubular drive shaft 12 project outwards (upwards as viewed in FIG. 1) from the control portion 4 so that the other ends thereof are positioned outside of the control portion 4 to be associated with the R-L control knob 5RL and the U-D control knob 5UD, respectively.

A cylindrical U-D bearing 13 in which the U-D tubular drive shaft 12 is fitted to be freely rotatable on the axis thereof is fixed at the base end of the U-D bearing 13 to a base of the supporting column 10 which is fixed to the internal main frame 50 of the control portion 4. The U-D bearing 13 also serves as a pulley cover which covers the R-L pulley 9RL and the U-D pulley 9UD to prevent the control wires 6U and 6D and the control wires 6R and 6L from being disengaged from the U-D pulley 9UD and the R-L pulley 9RL, respectively.

Rotating the U-D tubular drive shaft 12 about the axis thereof (on the axis of the supporting column 10) causes the U-D pulley 9UD to rotate to thereby pull one of the control wires 6U and 6D in accordance the direction of rotation of the U-D tubular drive shaft 12. Likewise, rotating the R-L tubular drive shaft 11 about the axis thereof (on the axis of the supporting column 10) causes the R-L pulley 9RL to rotate to thereby pull one of the control wires 6R and 6L in accordance the direction of rotation of the R-L tubular drive shaft 11.

A substantially disk-shaped seating plate 16 that is integral with the U-D control knob 5UD is positioned thereon to close an outer open end of the internal space of the U-D control knob 5UD, and an outer end surface of a grooved rotational plate (relatively rotatable member) 17 made of metal which is formed integral with the U-D tubular drive shaft 12 is in sliding contact with an inner surface of the seating plate 16 to be freely rotatable on the axis of the grooved rotational plate 17.

Figure 3:
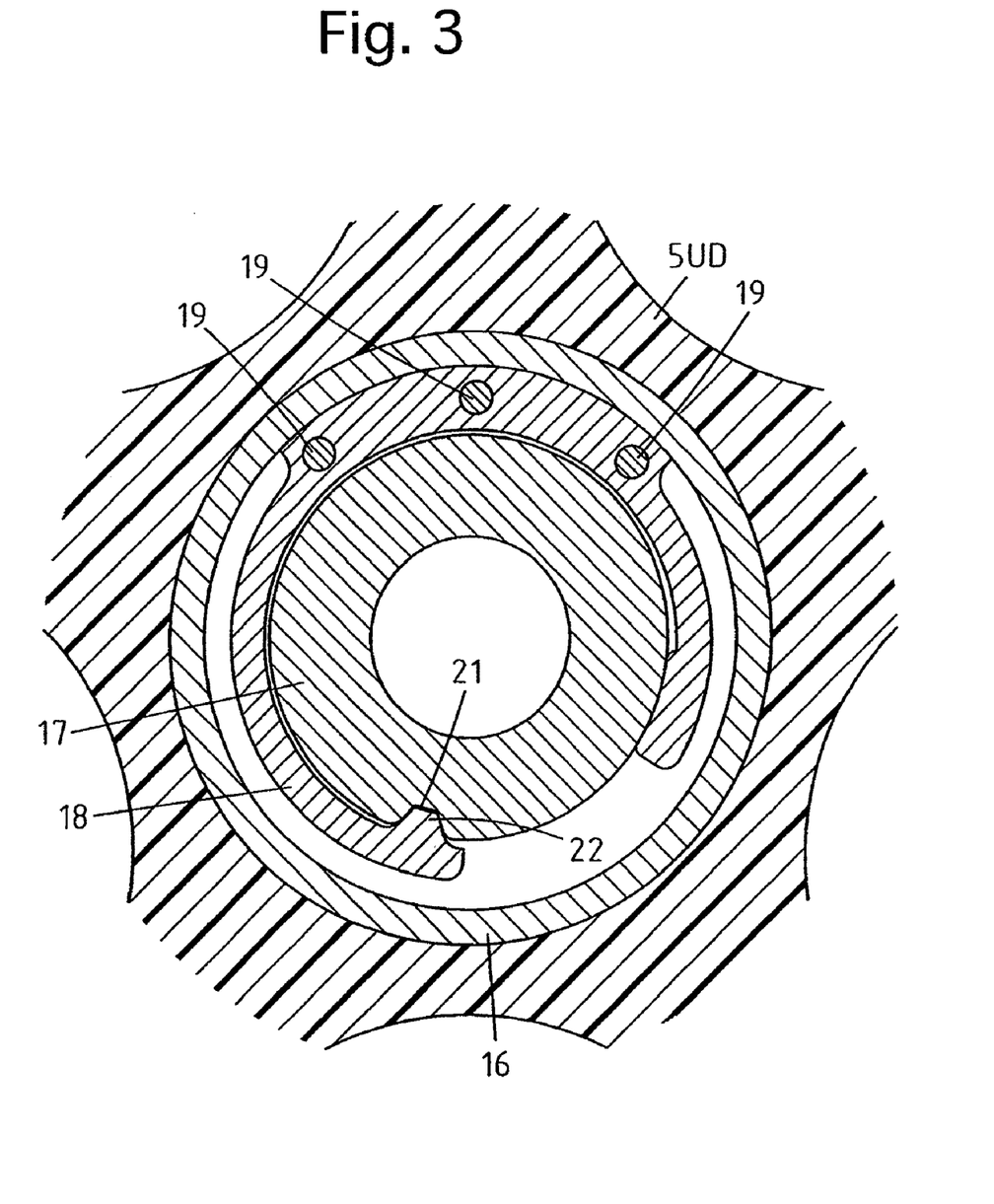
FIG. 3 is a cross sectional view of a torque limiting mechanism of the endoscope (taken along a III-III line in FIG. 1)

As shown in FIG. 3 that shows a cross sectional view taken along III-III line in FIG. 1, the grooved rotational plate 17, the outer edge of which is formed in a circular shape as a whole, is provided on a part of an outer peripheral surface thereof with an engaging groove (notch) 21. An arc-shaped spring engaging arm (relatively rotatable member) 18 made of a resilient material is fixed at a base end portion thereof to the seating plate 16 by three set crews 19 to be positioned around an outer periphery of the grooved rotational plate 17. The spring engaging arm 18 is provided at a free end thereof with an engaging lug 22 which projects radially inwards to be freely capable of being engaged in and disengaged from the engaging groove 21 of the grooved rotational plate 17.

When no external force is applied to the spring engaging arm 18, the spring engaging arm 18 is set in a state shown in FIG. 3 where the engaging lug 22 is engaged in the engaging groove 21 of the grooved rotational plate 17. The spring engaging arm 18 in this state can freely rotate integrally with the seating plate 16 about the axis of the thereof, and the engaging lug 22 remains engaged in the engaging groove 21 of the grooved rotational plate 17 when a torque exerted on the U-D control knob 5UD is equal to or less than a predetermined torque.

Accordingly, when the U-D control knob 5UD is manually rotated, the spring engaging arm 18 rotates with the seating plate 16 to thereby cause the grooved rotational plate 17 to rotate, so that the rotational control force exerted on the U-D control knob 5UD is transmitted to the control wires 6U and 6D via the U-D tubular drive shaft 12 and others.

Upon an excessive control force exceeding the aforementioned predetermined torque being exerted on the U-D control knob 5UD, the spring engaging arm 18 is resiliently deformed to make the engaging lug 22 disengaged from the engaging groove 21 of the grooved rotational plate 17 so that the grooved rotational plate 17 does not rotate with the seating plate 16 even if the seating plate 16 rotates, which prevents the U-D tubular drive shaft 12 from being rotated by an operation of the U-D control knob 5UD.

In this manner, a safety torque limiting mechanism for the case where an excessive force exceeding the predetermined torque is exerted on the U-D control knob 5UD includes the grooved rotational plate 17, the spring engaging arm 18, the engaging groove 21, the engaging lug 22, and is installed in an internal space of the U-D control knob 5UD.

Reference numerals 30 through 38 shown in FIG. 1 designate elements of a U-D bent state holding mechanism which exerts frictional resistance on the rotating operation of the bendable portion U-D control mechanism to hold the bendable portion U-D control mechanism (which includes the U-D control knob 5UD, the U-D tubular drive shaft 12 connected to the U-D control knob 5UD, the U-D pulley 9UD) at any given rotation position. The U-D bent state holding mechanism is accommodated and arranged in an internal space of the U-D control knob 5UD and can operate to exert friction on the rotating operation of the bendable portion U-D control mechanism and to stop exerting the same thereon.

Figure 4:
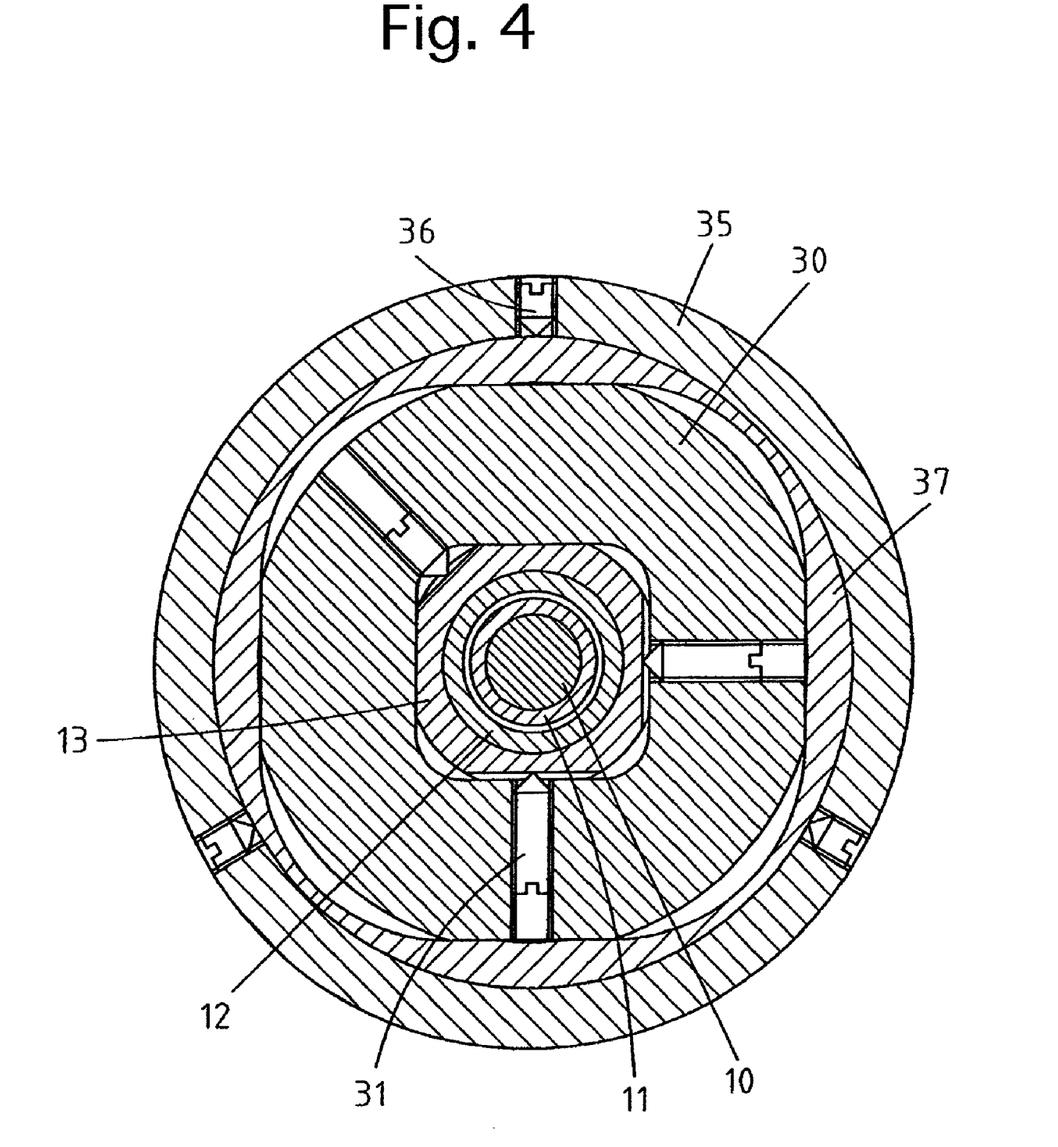
FIG. 4 is a cross sectional view taken along a IV-IV line shown in FIG. 1.
Figure 5:
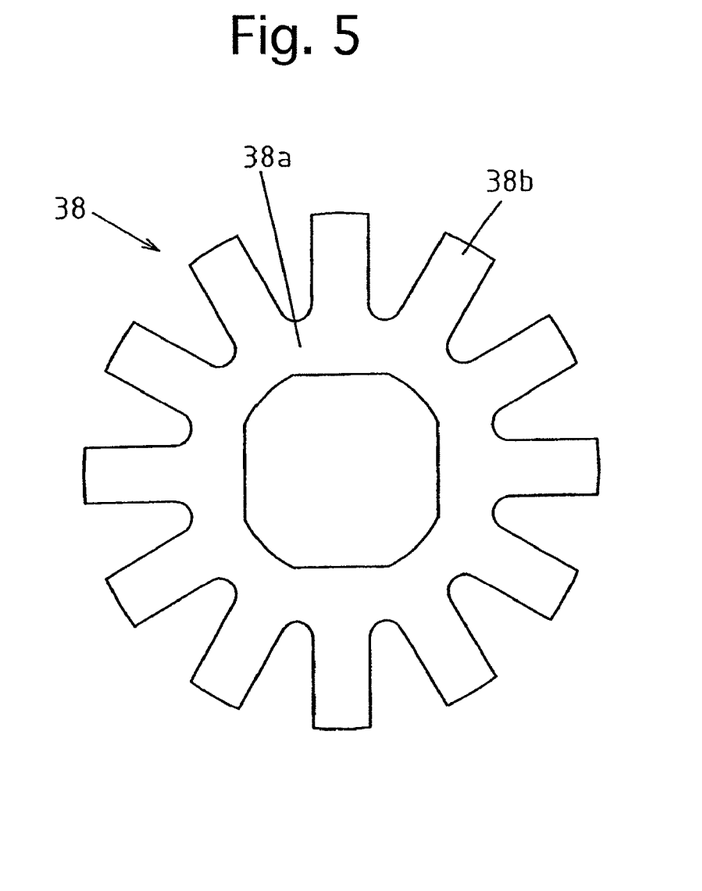
FIG. 5 is a plan view of a radial plate spring provided as an element of the bent state holding mechanism of the endoscope.

As also shown in FIG. 4 that shows a cross sectional view taken along IV-IV line shown in FIG. 1, an immovable base 30 is secured to the cylindrical U-D bearing 13 (having been fixed to the main frame 50) in the vicinity of the top end thereof by set screws 31.

The U-D bent state holding knob 7UD is fitted on an outer peripheral surface of the U-D bearing 13 to be freely rotatable thereon. A male screw ring 32 having a male screw thread on an outer peripheral surface thereof is provided in a central portion of the male screw ring 32 with a polygonal-shaped hole while the U-D bent state holding knob 7UD is provided in a central portion thereof with a corresponding polygonal-shaped shaft portion which is fixedly fitted in the polygonal-shaped hole of the male screw ring 32 so that the male screw ring 32 rotates with the U-D bent state holding knob 7UD.

The range of rotation of the U-D bent state holding knob 7UD (the male screw ring 32) is defined by an arc-shaped groove 33 which is formed in the male screw ring 32 and a stop pin 34 which projects from the immovable base 30 to be engaged in the arc-shaped groove 33.

A female screw ring (fixing member) 35 is screw-engaged with the male screw ring 32. A female screw thread of the female screw ring 35 which is screw-engaged with the male screw thread of the male screw ring 32 is formed on a substantially lower-half of the inner peripheral surface of the female screw ring 35. The letter "N" shown in FIG. 3 designates the portion of engagement between the female screw thread of the female screw ring 35 and the male screw thread of the male screw ring 32. A metal disk (frictional resistance producing member/annular friction member) 37 is positioned inside of an upper half portion of the female screw ring 35 and fixed integrally thereto by a set screw 36.

The metal disk 37 is made of, e.g., brass, stainless steel or the like. As shown in FIG. 4, the metal disk 37 has a substantially square central hole, and an inner peripheral surface of the metal disk 37 is partly engaged in an outer peripheral surface of the immovable base 30 at substantially equi-angular intervals of 90 degrees in a manner to allow the metal disk 37 to move in the axial direction relative to the immovable base 30 while preventing the metal disk 37 from rotating about the axis thereof relative to the immovable base 30. Therefore, the female screw ring 35, which moves with the metal disk 37, is also freely movable in the axial direction though not rotatable about the axis of the female screw ring 35.

Reference numeral 38 shown in FIG. 1 designates a radial plate spring (frictional resistance producing member) made of a resilient metal plate such as a spring stainless steel. The radial plate spring 38 is provided with a ring portion 38*a* and a plurality of radial projections (radial leaf springs) 38*b* which are formed integral with the ring portion 38*a* to project radially outwards from the ring portion 38*a*. The radial plate spring 38 is formed in a flat shape as a whole, and the ring portion 38*a* is provided at a center thereof with a substantially square hole.

The radial plate spring 38 is engaged at the square hole thereof with a portion of the U-D tubular drive shaft 12 in the vicinity of the upper end thereof to rotate with the U-D tubular drive shaft 12 about the axis thereof. The back of the ring portion 38*a* of the radial plate spring 38 is in contact with the upper end surface of the immovable base 30 to be supported thereby.

An annular surface of the metal disk 37 which is located at a position facing the plurality of radial projections 38*b* of the radial plate spring 38 is formed as a pressure surface 37*a* which is brought to be pressed obliquely against upper flat surfaces of the plurality of radial projections 38*b*. More specifically, the pressure surface 37*a* of the metal disk 37 is formed in an umbrella-like beveled shape (truncated conical shape) which approaches the plurality of radial projections 38*b* in radially directions from the radially inside to the radially outside of the pressure surface 37*a*. While the flat surfaces of the radial projections 38*b* are located in a plane normal to an axis of the radial plate spring 38 (the metal disk 37), the pressure surface 37*a* of the metal disk inclined with respect to the plane so that the center (top) of the pressure surface in the form of the truncated conical shape is the farthest from the plane.

With this structure, manually rotating the U-D bent state holding knob 7UD causes the male screw ring 32 to rotate with the U-D bent state holding knob 7UD about the axis of the male screw ring 32. This rotation of the male screw ring 32 causes the female screw ring 35, which is screw-engaged with the male screw ring 32 at the portion of engagement N, and the metal disk 37, which is integral with the female screw ring 35, to move in the axial direction without rotating about the axis of the supporting column 10, so that the distance between the radial plate spring 38 and the pressure surface 37*a* of the metal disk 37 changes.

When the U-D bent state holding knob 7UD is at one of the opposite ends (free-state end) of the range of rotation of the U-D bent state holding knob 7UD, a slight clearance is formed between the radial plate spring 38 and the pressure surface 37*a* of the metal disk 37 as shown in FIG. 1 so that the radial plate spring 38 and the metal disk 37 are not in sliding contact with each other. Therefore, the metal disk 37 and the radial plate spring 38 exert no frictional resistance on the rotating operation of the bendable portion control mechanism (composed of the U-D control knob 5UD, the U-D tubular drive shaft 12, the U-D direction pulley 9UD and others) for pulling the upward-direction control wire 6U and the downward-direction control wire 6D.

Figure 7:
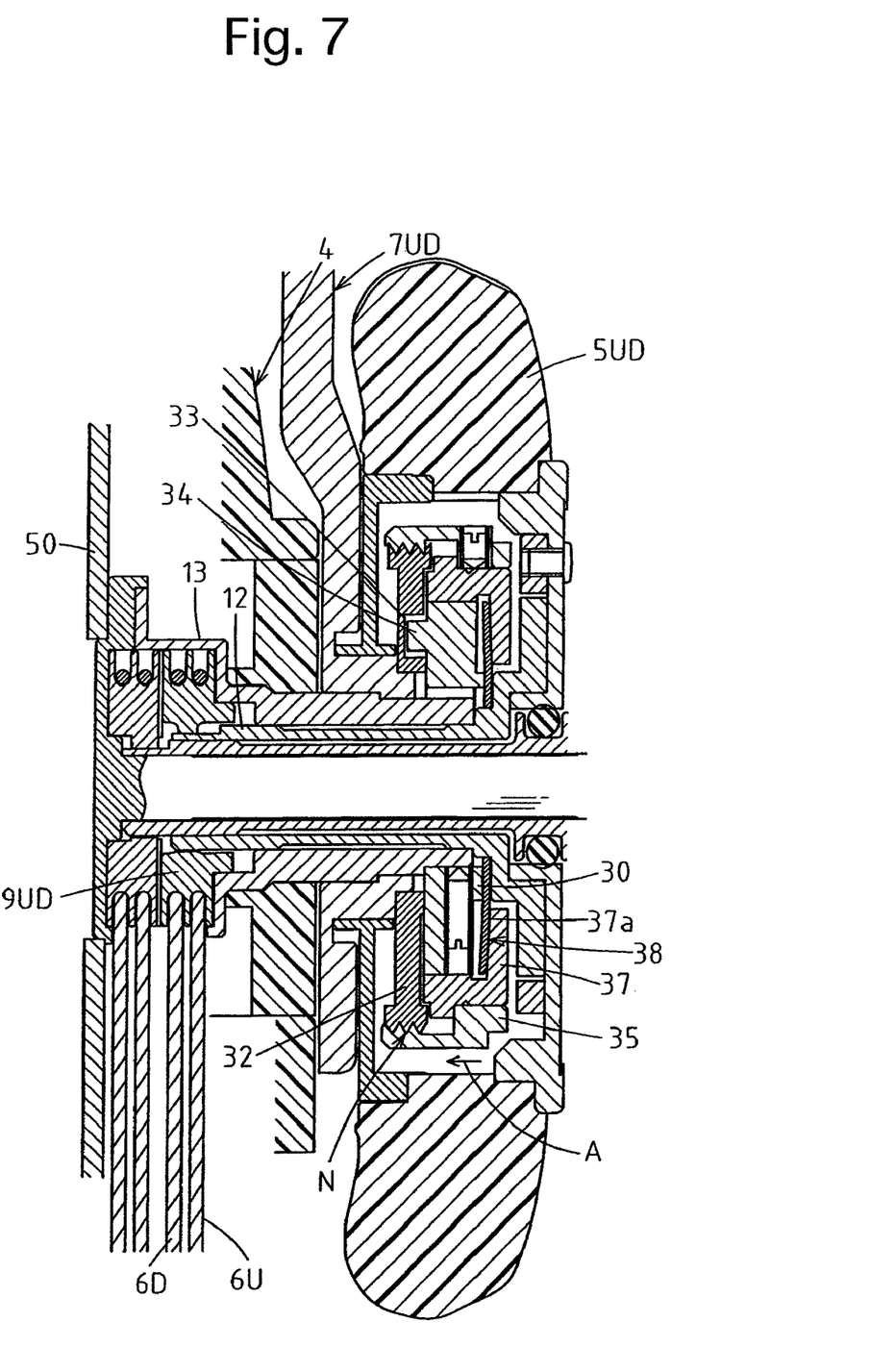
FIG. 7 is a view similar to that of FIG. 1 and illustrates an operational state of the bent state holding mechanism of the endoscope.
Figure 8A:
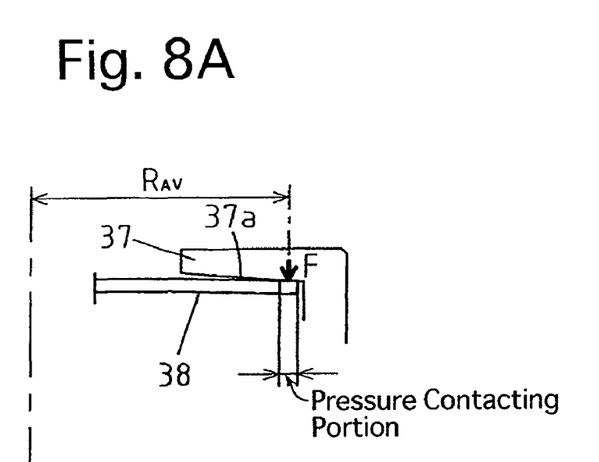
FIG. 8A is a longitudinal cross sectional view of a portion of the bent state holding mechanism of the endoscope, showing a process of variation of the state where the radial plate spring is pressed against a metal disk of the bent state holding mechanism.
Figure 8B:
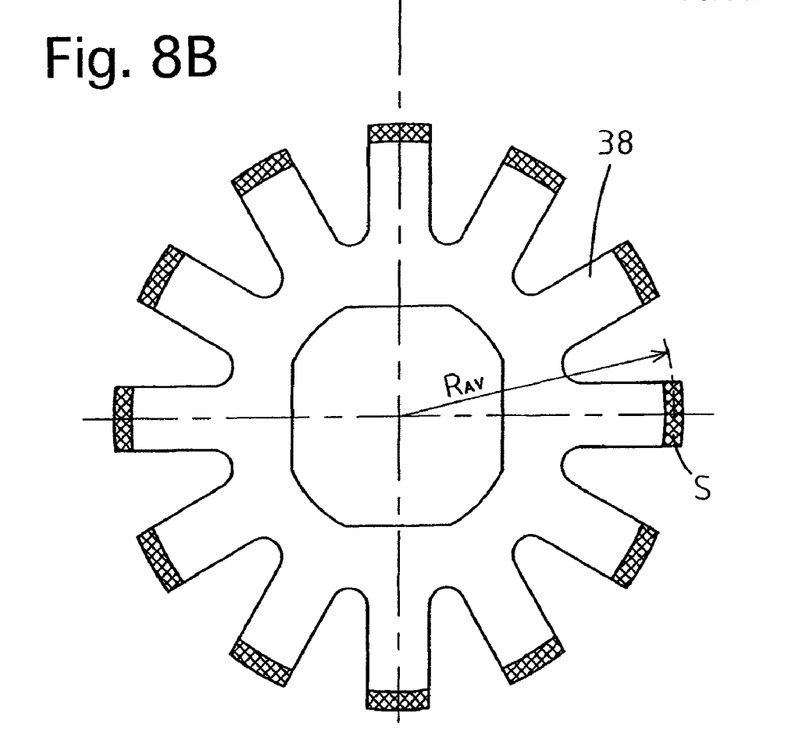
FIG. 8B is a plan view of the radial plate spring shown in FIG. 8A.
Figure 9A:
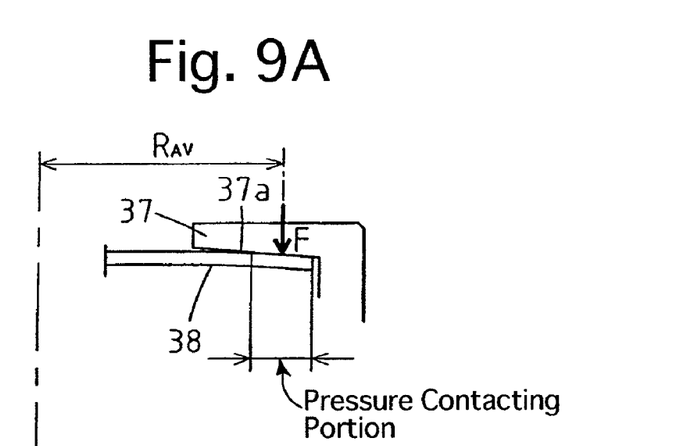
FIG. 9A is a longitudinal cross sectional view of a portion of the bent state holding mechanism of the endoscope, showing a process of variation of the state where the radial plate spring is pressed against the metal disk of the bent state holding mechanism.
Figure 9B:
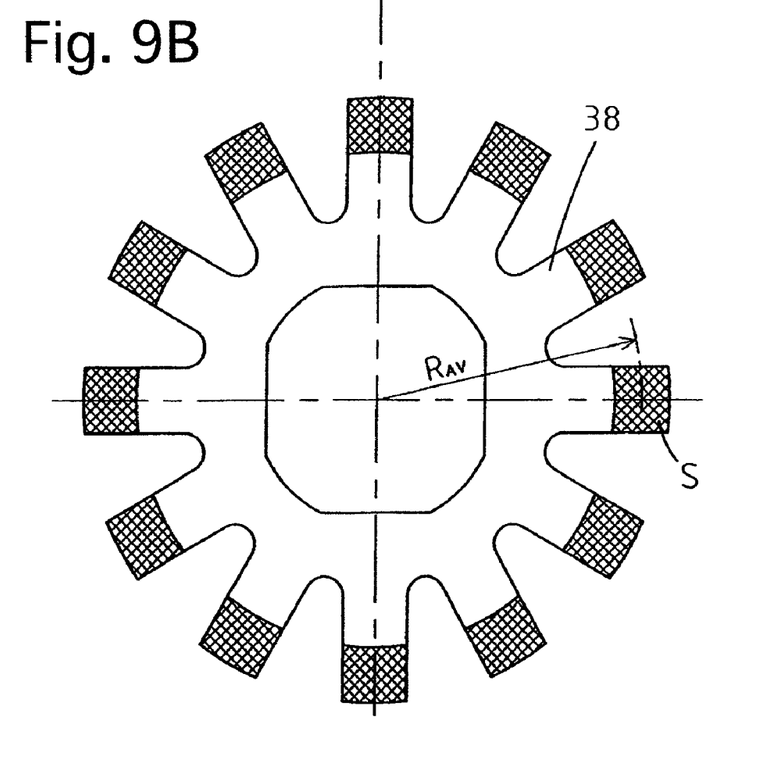
FIG. 9B is a plan view of the radial plate spring shown in FIG. 9A.

Rotating the U-D bent state holding knob 7UD to the other end (lock end) of the range of rotation of the U-D bent state holding knob 7UD causes the metal disk 37 to move in a direction shown by the arrow A in FIG. 7, thus causing the pressure surface 37*a* of the metal disk 37 to be pressed against the radial plate spring 38 so that the radial plate spring 38 and the metal disk 37 come in sliding contact with each other. The frictional resistance caused by this sliding contact acts on the rotating operation of the bendable portion control mechanism for pulling the upward-direction control wire 6U and the downward-direction control wire 6D.

In this operation of the U-D bent state holding knob 7UD, if the U-D bent state holding knob 7UD is operated to rotate slightly from the free state shown in FIG. 1, firstly the pressure surface 37a of the metal disk 37 comes into contact with radially outermost portions of the plurality of radial projections 38b so that a slight frictional resistance is produced between the pressure surface 37a and the plurality of radial projections 38b and a further rotation of the U-D bent state holding knob 7UD in the same rotation direction toward the lock position causes the area of the portions of the plurality of radial projections 38b which are pressed against the pressure surface 37a to increase gradually in radially inward directions to thereby increase the frictional resistance produced between the pressure surface 37a and the plurality of radial projections 38b.

Subsequently, rotating the U-D bent state holding knob 7UD back to the free-state position shown in FIG. 1 causes the radial plate spring 38 to return to its flat state in which the radial plate spring 38 is not pressed against the metal disk 37. In this manner, one can freely switch between an engaged state in which the plurality of radial projections 38b of the radial plate spring 38 and the pressure surface 37a are pressed against each other and a disengaged state in which the plurality of radial projections 38b of the radial plate spring 38 and the pressure surface 37a are disengaged from each other, and between these two states one can continuously vary the amount of the pressure contact between the plurality of radial projections 38b of the radial plate spring 38 and the pressure surface 37a of the metal disk 37.

In the course of the change in magnitude of frictional resistance in this manner, the portion of the radial plate spring 38 which is brought to be pressed against the pressure surface 37a of the metal disk 37 that is formed in an umbrella-like beveled shape (truncated conical shape) is resiliently deformed along the beveled surface of the pressure surface 37a.

FIGS. 8A and 9A, and 8B and 9B are longitudinal cross sectional views of a portion of the bent state holding mechanism of the endoscope and plan views of the radial plate spring 38, respectively, showing the process of variation of the state of pressure contact between the pressure surface 37a of the metal disk 37 and the radial plate spring 38. As the area S (see FIGS. 9A and 9B) on each radial projection 38 which is pressed against the pressure surface 37a increases, an average turning radius $R_{AV}$ of the pressure contacting portion between the radial projection 38 and the pressure surface 37a decreases (note that an average turning radius corresponding to the average turning radius $R_{AV}$ does not change in a conventional bent state holding mechanism in which opposed flat surfaces are fully pressed against with each other).

Consequently, in the present embodiment of the bent state holding mechanism in which the average turning radius $R_{AV}$ of the pressure contacting portion gradually decreases, the variation of brake torque is milder than that in a conventional bent state holding mechanism in which an average turning radius corresponding to the average turning radius $R_{AV}$ does not change because in the present invention the following equation is satisfied:

$$BT = \mu \times F \times R_{AV}$$

wherein BT represents the brake torque which acts on the U-D bent state holding knob 7UD;

μ represents the friction factor; and

F represents the force applied to the pressure surface in a direction orthogonal to the pressure surface.

Moreover, an adjustment operation during assembly of the endoscope can be easily performed with precision. Furthermore, brake torque deterioration due to age is minimal and high durability is achieved.

In this manner, the frictional resistance producing members which rotate relative to each other to exert frictional resistance on the rotating operation of the bendable portion U-D control mechanism (which is composed of the U-D control knob 5UD, the U-D tubular drive shaft 12, the U-D pulley 9UD and others) consists of only the metal disk 37 and the radial plate spring 38, and accordingly, each of such frictional resistance producing members can be made thin.

Consequently, the U-D bent state holding mechanism that is composed of the elements 30 through 38 can be made thin to be installed in an internal space of the U-D control knob 5UD, which makes it possible to miniaturize the U-D control knob 5UD to thereby improve the operability thereof and to install the torque limiting mechanism (which includes the grooved rotational plate 17, the spring engaging arm 18, the engaging groove 21, the engaging lug 22), or the like, in an internal space of the U-D control knob 5UD with no need to increase the size of the U-D control knob 5UD. Additionally, the two frictional resistance producing members (37 and 38) are resistant to heat, aging and the like, and high durability is achieved.

Since static friction is assertively greater than dynamic friction at points of contact between metals, the pressure contact between the metal disk 37 and the radial plate spring 38 makes it possible to lock the U-D bent state holding knob 7UD securely without yielding the reactive force received from the upward-direction control wire 6U and the downward-direction control wire 6D.

Subsequently, if operated to rotate from this state, the U-D bent state holding knob 7UD can be lightly operated with a little frictional resistance once the U-D bent state holding knob 7UD starts moving, and at the subsequent stop position the U-D bent state holding knob 7UD is again locked securely without yielding the reactive force received from the upward-direction control wire 6U and the downward-direction control wire 6D.

Figure 6:
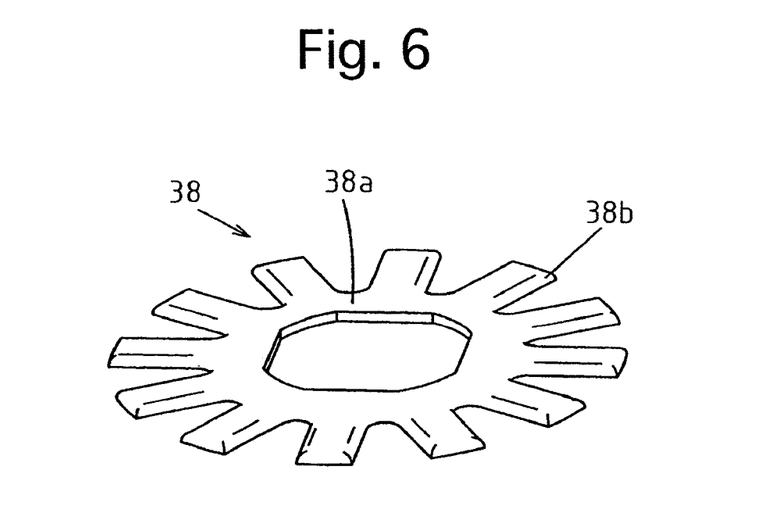
FIG. 6 is a perspective view of the radial plate spring shown in FIG. 5.

Note that at least the edges of each radial projection 38b of the radial plate spring 38 which are brought to be pressed against the pressure surface 37a of the metal disk 37 are all chamfered to be smoothly-curved edges so that each radial projection 38b can come in contact with the metal disk 37 smoothly (see FIG. 6). Moreover, since the metal disk 37 comes in sliding contact with the radial plate spring 38 from radially outermost portions of the plurality of radial projections 38b whenever the metal disk 37 is brought to be pressed against the radial plate spring 38, the magnitude of the frictional resistance which occurs by pressure contact between the radial plate spring 38 and the metal disk 37 does not change suddenly by a large amount, so that an appropriate frictional resistance is exerted on the rotating operation of the bendable portion control mechanism with stability.

Figure 10:
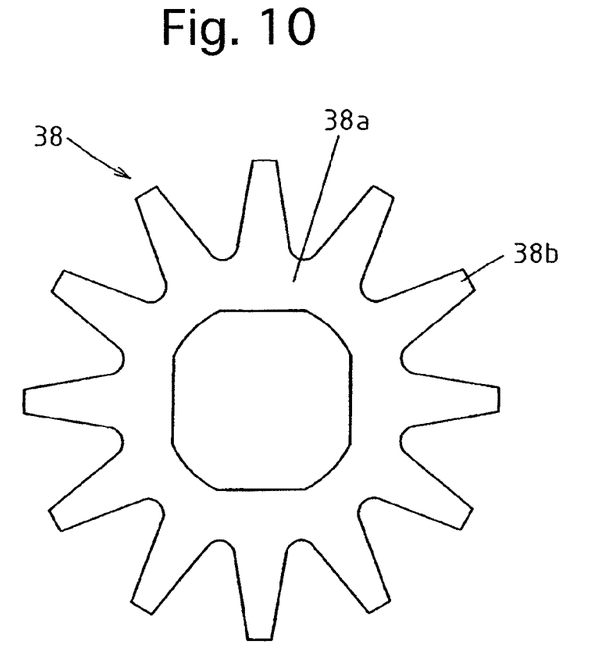
FIG. 10 is a plan view of a second embodiment of the radial plate spring.
Figure 11:
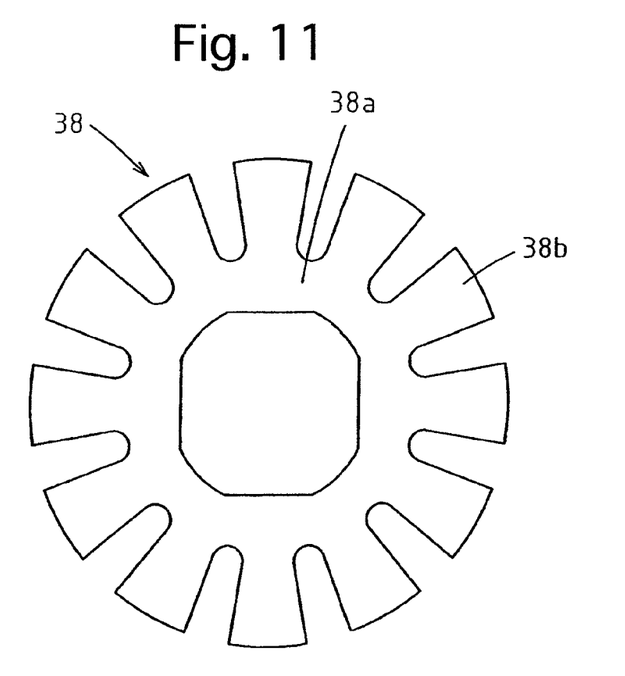
FIG. 11 is a plan view of a third embodiment of the radial plate spring.
Figure 12:
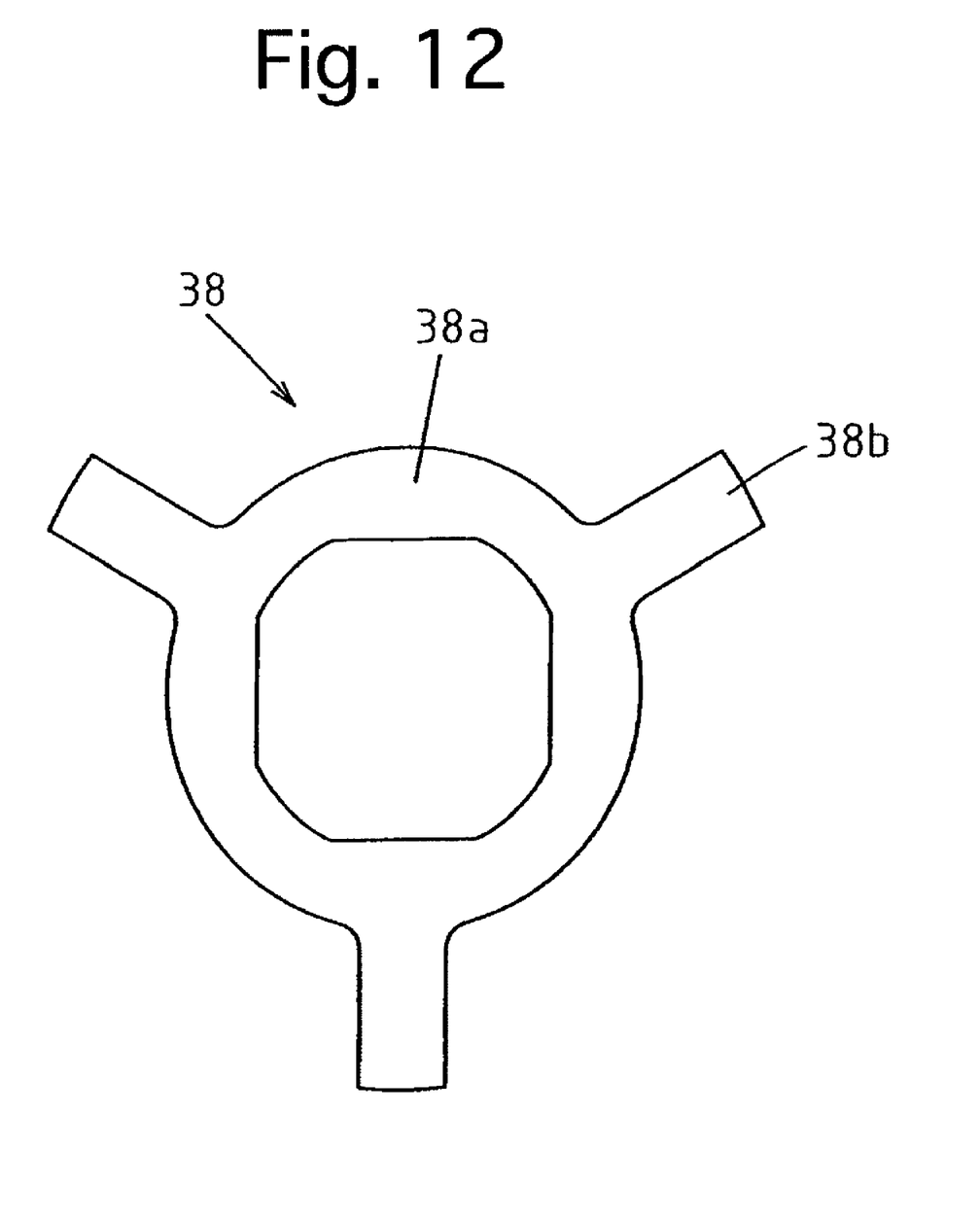
FIG. 12 is a plan view of a fourth embodiment of the radial plate spring.

The present invention is not limited solely to the above described particular embodiment. For instance, as shown in FIGS. 10 through 12 that show other embodiments of the radial plate springs, the number of the radial projections 38b and the shape of the radial plate spring 38 are optional.

In addition, it is possible that the radial plate spring 38 be formed in an umbrella-like beveled shape (truncated conical shape) as a whole while the pressure surface 37a of the metal plate 37 be formed in a flat shape, and it is further possible that the radial plate spring 38 be mounted to an irrotational portion while the metal disk 37 be mounted to a rotational portion (the U-D tubular drive shaft 12). Additionally, it is possible that the bent state holding mechanism according to the present invention be installed in the R-L control knob 5RL.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A bent state holding mechanism for an endoscope which includes a control portion and an insertion portion extending from said control portion, said insertion portion having a bendable portion at a distal end thereof, comprising:
    a bendable portion control mechanism provided on said control portion, which is operated to bend said bendable portion, and
    at least two frictional resistance producing members which rotate relative to each other upon operation of said bendable portion control mechanism, to exert a frictional resistance for holding said bendable portion at any operated position,
    wherein said two frictional resistance producing members include a radial plate spring made of resilient metal which includes a ring portion and a plurality of radial projections which project radially outwards from an outer periphery of said ring portion,
    wherein said radial plate spring rotates with said bendable portion control mechanism about an axis of rotation; and
    an annular friction member having a pressure surface which is brought to be pressed obliquely against flat surfaces of said plurality of radial projections,
    wherein said annular friction member is engaged with a fixing member of said control portion to be prevented from rotating relative to said control portion.

2. The bent state holding mechanism according to claim 1, wherein said radial plate spring is formed in a flat shape as a whole, and
    wherein said pressure surface of said annular friction member is formed in an umbrella-like beveled shape.

3. The bent state holding mechanism according to claim 1, wherein said radial plate spring is formed in an umbrella-like beveled shape as a whole, and
    wherein said pressure surface of said annular friction member is formed in a flat shape.

4. The bent state holding mechanism according to claim 1, wherein at least edges of said plurality of radial projections which are pressed against said pressure surface of said annular friction member are chamfered.

5. The bent state holding mechanism according to claim 1, further comprising a bent state holding device which is operated to switch between an engaged state in which said plurality of radial projections and said pressure surface of said annular friction member are pressed against each other and a disengaged state in which said plurality of radial projections and said pressure surface of said annular friction member are disengaged from each other.

6. The bent state holding mechanism according to claim 5, wherein the amount of pressure contact between said plurality of radial projections and said annular friction member can be varied by an operation of said bent state holding device.

7. The bent state holding mechanism according to claim 6, wherein as said amount of pressure contact between said plurality of radial projections and said annular friction member increases, said plurality of radial projections are resiliently deformed by a greater amount while the area on portions of said plurality of radial projections which are pressed against said pressure surface of said annular friction member gradually increases in radially inward directions from radially outermost portions of said plurality of radial projections.

8. The bent state holding mechanism according to claim 1, wherein said bendable portion control mechanism comprises a bendable portion control knob for controlling said bendable portion, said bent state holding mechanism being installed in an internal space of said bendable portion control knob.

9. The bent state holding mechanism according to claim 1, wherein said annular friction member comprises a metal disk.

10. The bent state holding mechanism according to claim 1, wherein said endoscope includes a control wire, a distal end of which is fixed to said bendable portion and which is extended to said control portion through said insertion portion.

11. The bent state holding mechanism according to claim 8, wherein said bendable portion control device comprises a torque limiting mechanism for allowing a torque exerted on said bendable portion control mechanism to be transmitted to said bendable portion when said torque is equal to or less than a predetermined torque, and for preventing said torque from being transmitted to said bendable portion when said torque exceeds said predetermined torque, said torque limiting mechanism being installed in an internal space of said bendable portion control knob.

12. The bent state holding mechanism according to claim 5, wherein said bendable portion control mechanism comprises a bendable portion control knob for controlling said bendable portion, and
    wherein said bent state holding device includes a bent state holding knob positioned so as to be capable of being operated to rotate coaxially with said bendable portion control knob.

13. The bent state holding mechanism according to claim 6, wherein when an amount of friction between said plurality of radial projections and said annular friction member is increasing, an area of said pressure surface becomes larger, and an average turning radius becomes smaller.

* * * * *